(12) United States Patent
Silvis

(10) Patent No.: US 6,505,524 B1
(45) Date of Patent: *Jan. 14, 2003

(54) MIXING SYSTEM AND METHOD

(75) Inventor: William M. Silvis, Ann Arbor, MI (US)

(73) Assignee: Horiba Instruments, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 385 days.

(21) Appl. No.: 09/114,332

(22) Filed: Jul. 13, 1998

(51) Int. Cl.$^7$ ................................................ G01N 1/00
(52) U.S. Cl. ................................................ 73/863.03
(58) Field of Search ...................... 73/863.02, 863.03, 73/23.31, 23.32, 864.73; 137/88, 3

(56) References Cited

U.S. PATENT DOCUMENTS

| | | | |
|---|---|---|---|
| 3,699,814 A | | 10/1972 | Kaufman |
| 3,817,100 A | | 6/1974 | Anderson et al. |
| 4,494,209 A | * | 1/1985 | Agarwal |
| 4,555,931 A | * | 12/1985 | Amimoto et al. ........... 73/23.31 |
| 4,823,591 A | | 4/1989 | Lewis |
| 5,419,178 A | * | 5/1995 | Decker et al. ............. 73/23.31 |
| 5,423,228 A | | 6/1995 | Budd et al. |
| 5,469,731 A | * | 11/1995 | Decker et al. ............ 73/863.03 |
| 5,569,838 A | | 10/1996 | Broedel et al. |
| 5,691,464 A | * | 11/1997 | Cao ........................... 73/23.31 |
| 5,756,360 A | * | 5/1998 | Harvey et al. ............ 73/863.03 |
| 5,852,227 A | * | 12/1998 | Garthe ....................... 73/23.32 |

FOREIGN PATENT DOCUMENTS

WO     WO 97/31265     8/1997

* cited by examiner

Primary Examiner—Robert Raevis
(74) Attorney, Agent, or Firm—Brooks & Kushman P.C.

(57) ABSTRACT

A mixing system with proportional dilution gas sampling, and associated proportional dilution gas sampling methods are provided. The mixing system includes a mixing portion, a gaseous inlet, a dilution inlet, and a mixture outlet. A flow meter in flow communication with the dilution inlet has an output indicative of the dilution gas flow rate. A dilution sample line in flow communication with the dilution inlet collects samples of the dilution gas. A dilution sample flow controller along the dilution sample line is applicable to vary the dilution sample flow rate through the dilution sample line. Control logic receives the flow meter output, processes the flow meter output, and operates the dilution sample flow controller to vary the dilution sample flow rate. The dilution sample flow rate is varied in response to variations in the dilution gas flow rate such that the dilution sample flow rate tracks a value which is substantially proportional to the dilution gas flow rate.

18 Claims, 2 Drawing Sheets

MIXING SYSTEM AND METHOD

TECHNICAL FIELD

The present invention relates to measurement and dilution techniques for analysis of gaseous constituents.

BACKGROUND ART

A gas diluting and testing apparatus is used to analyze, among other things, vehicular exhaust. The apparatus uses a mixing system to dilute the exhaust gases so that the moisture content of the gases is sufficiently reduced in order to minimize errors due to condensation. One example of an existing mixing system is the Constant Volume Sampler (CVS).

The CVS has been used for over twenty-five years to sample the emissions from automobiles. It is the device used for all automotive emissions tests that are the basis for the certification that vehicles sold in the United States are compliant with the Clean Air Act.

As vehicles become cleaner, their emissions become more difficult to measure accurately. In particular, because the basic operation of the CVS involves diluting the vehicle's exhaust with air that may also contain small amounts of the pollutants to be measured, it becomes important to be able to accurately separate out the contributions from this source and the contribution from the vehicle under test.

Historically, this ambient contribution has been corrected for by taking a sample of the diluent air at the same time that a sample of the diluted vehicle exhaust is taken. This measurement, with some modifications to account for the different conditions of sampling, is subtracted from the measurement made of the diluted exhaust. However, this method makes some assumptions about the stability of the background pollutants and about the combustion process. Because these assumptions are not completely true, the errors caused by these assumptions have become significant as vehicles have become cleaner.

Referring to FIG. 1, a conventional CVS is generally indicated at 10. CVS 10 has a mixing portion 12, a gaseous inlet 14, a dilution inlet 16, and a mixture outlet 18. A dilution sample line 20, a needle valve 22 and a pump 24 cooperate to a bag 26 with dilution gas.

Raw exhaust from the vehicle under test enters gaseous inlet 14 and is mixed with dilution air. The mixed gases are drawn through a main venturi 30 by a blower 32. Main venturi 30 is sonic, or choked, and meters and measures the flow of the combined gases. A mixture sample line 34 connects to mixture outlet 18 through a smaller, sample venturi 36 also operated in sonic or choked condition. A pump 38 cooperates with sample venturi 36 to fill a sample bag 40 with the mixed gases for later analysis.

Because there are measurable amounts of the pollutants in the dilution gas used to dilute the exhaust gases, the dilution gas sample in bag 26, which is collected through pump 24 and needle valve 22 at a nominally constant flow rate, is analyzed. Typically, the pollutant concentration in the dilution bag 26 and in the sample bag 40 are used to determine pollutant emissions according to the following known formula:

$$\text{grams}_C = \text{density}_C * ([C]_{sam\_bag} - [C]_{amb\_bag}(1 - 1/DF)) * V_{cvs}$$

wherein $\text{grams}_C$ is the gaseous constituent content in the test gas, $\text{density}_C$ is the density of the gaseous constituent, $[C]_{sam\_bag}$ is the concentration of the gaseous constituent in the gaseous mixture sample, $[C]_{amb\_bag}$ is the concentration of the gaseous constituent in the dilution gas sample, DF is the theoretical dilution factor (determined as indicated below), and $V_{CVS}$ is the total volume of the gaseous mixture drawn through the system.

The dilution factor, DF, is the ratio of the total volume of gases taken through the CVS to the volume of exhaust gases from the test vehicle. In the conventional CVS, the dilution factor DF is specified by the following theoretical formula:

$$DF = \frac{x}{\frac{x + \frac{y}{2} + 3.76\left(x + \frac{y}{4} - \frac{z}{2}\right)}{[CO_2]_{sam\_bag} + [CO]_{sam\_bag} + [HC]_{sam\_bag}}}$$

wherein x, y, and z come from the composition of the fuel, which is considered to have the chemical formula $C_xH_yO$. Further, in the above formula $[CO_2]_{sam\_bag}$ is the concentration of carbon dioxide in the gaseous mixture sample, $[CO]_{sam\_bag}$ is the concentration of carbon monoxide in the gaseous mixture sample, and $[HC]_{sam\_bag}$ is the concentration of hydrocarbons in the gaseous mixture sample.

Although conventional mixing systems of the CVS type have been used in many applications which have been commercially successful, it is to be appreciated that as the amounts of pollutants in vehicular exhaust decrease, the assumptions made for the conventional CVS have an increasing effect on the accuracy of the testing. Because the contribution of the dilution gas to the overall pollutant content of the gaseous mixture sample is becoming more and more significant in the calculation of exhaust gas pollutant content, there is a need for an improved mixing system that overcomes the problems and limitations of the prior art.

DISCLOSURE OF INVENTION

It is, therefore, an object of the present invention to provide a mixing system utilizing proportional dilution gas sampling, and thereby increasing the accuracy of the testing program.

It is a further object of the present invention to provide proportional dilution gas sampling methods.

In carrying out the above objects and other objects and features of the present invention, a mixing system for diluting gases is provided. The mixing system comprises a mixing portion, gaseous inlet, a dilution inlet, and a mixture outlet. The gaseous inlet is in flow communication with the mixing portion and receives the test gases. The dilution inlet is in flow communication with the mixing portion and receives the dilution gas. The mixture outlet is also in flow communication with the mixing portion.

The mixing system further comprises a flow meter in flow communication with the dilution inlet, a dilution sample line in flow communication with the dilution inlet, and a dilution sample flow controller along the dilution sample line. The flow meter has an output indicative of a dilution gas flow rate. The dilution inlet collects samples of the dilution gas; and, the dilution sample flow controller is operable to vary a dilution sample flow rate through the dilution sample line.

Control logic receives the flow meter output, and processes the flow meter output. The control logic operates the dilution sample flow controller to vary the dilution sample flow rate in response to variations in the dilution gas flow rate. The dilution sample flow rate is varied such that the dilution sample flow rate tracks a value which is substantially proportional to the dilution gas flow rate.

Further, in carrying out the present invention, a method for determining a gaseous constituent content in a test gas using a mixing system is provided. The method comprises mixing a dilution gas with the test gas to produce a gaseous mixture. The dilution gas has a dilution gas flow rate. The gaseous mixture has a gaseous mixture flow rate. The method further comprises monitoring the dilution gas flow rate, and sampling the dilution gas at a dilution sampling rate that is substantially proportional to the dilution gas flow rate to obtain a dilution gas sample. The gaseous mixture is sampled to obtain a gaseous mixture sample. A gaseous constituent content in the gaseous mixture sample is determined; a gaseous constituent content in the dilution gas sample is also determined. The gaseous constituent content in the test gas is determined based on the gaseous constituent content in the gaseous mixture sample, and the gaseous constituent content in the dilution gas sample.

Still further, in carrying out the present invention, a method for operating a mixing system is provided. The method comprises mixing a diluting gas with a test gas to produce a gaseous mixture, monitoring the dilution gas flow rate, sampling the dilution gas at a dilution sampling rate that is substantially proportional to the dilution gas flow rate to obtain a dilution gas sample, and sampling the gaseous mixture to obtain a gaseous mixture sample.

The advantages associated with embodiments of the present invention are numerous. For example, a mixing system made in accordance with the present invention functions as a Constant Volume Sampler (CVS) with proportional dilution gas sampling. The proportional dilution gas sampling allows true calculation of gaseous constituent content in the dilution gas, avoiding the need for assumptions made in a conventional CVS that may result in inaccurate test results. Further, because the CVS of the present invention with proportional dilution gas sampling avoids assumptions made with a conventional CVS, the accuracy of the vehicle emissions measurement is increased. Additionally, embodiments of the present invention offer a cost savings for the filtering and conditioning of the dilution gas, and performance improvements and the lowering of sampling back-pressure on the vehicle exhaust pipe during vehicular emissions testing.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

Figure 1:
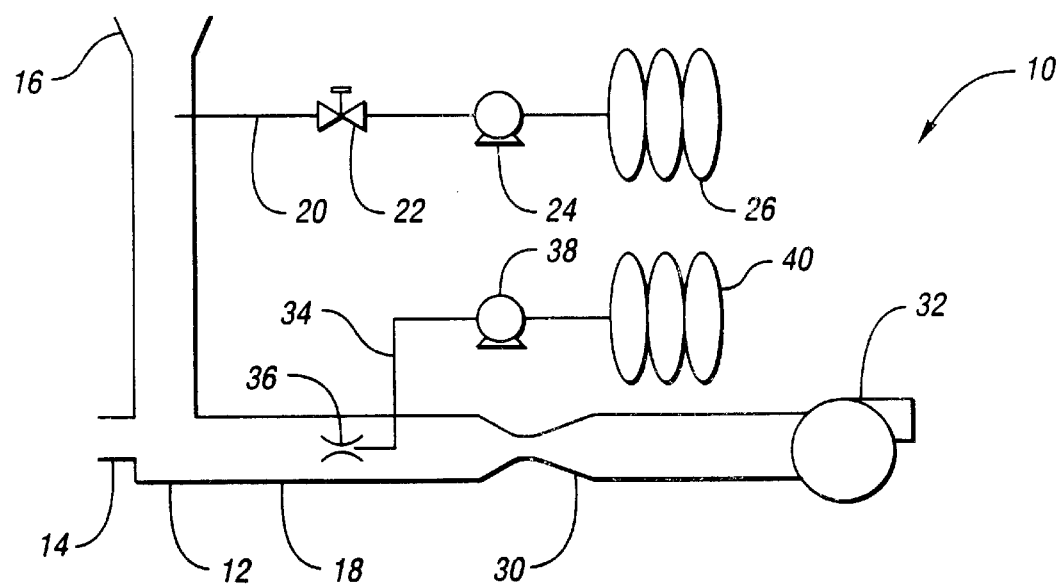
FIG. 1 is a schematic block diagram illustrating a conventional CVS with non-proportional dilution gas sampling.

With reference to FIG. 1, conventional CVS 10 is used to collect mixture samples, and gaseous constituent content is calculated as described previously.

It is to be appreciated that when developing embodiments of the present invention, the inventor performed detailed mathematical analysis on the conventional CVS 10. This detailed mathematical analysis, which was performed by the inventor to assist in recognizing the problems addressed by the present invention, is described below. Further, it is to be appreciated that the inventor has recognized problems with the prior art that are unobvious, but may be understood with reference to the below mathematical computations performed by the inventor.

There are two physical laws that describe the flow of the masses of gas in the CVS unit. There is the conservation of mass, or the continuity equation, and the flow balances of the converging streams. From the conservation of mass, each moment in time the mass of diluted pollutant must equal the mass coming from the vehicle plus the mass that comes in from the dilution air. Thus:

$$[C]_{sam} \cdot Q_{CVS} = [C]_{raw} \cdot Q_{ex} + [C]_{amb} \cdot Q_{amb}$$

The flow balance requires that:

$$Q_{CVS} = Q_{ex} + Q_{amb}$$

Because it is the pollutant from the vehicle that we wish to measure, combining and re-arranging these equations results in:

$$[C]_{raw} \cdot Q_{ex} = \left( [C]_{sam} \cdot Q_{CVS} - [C]_{amb}\left(1 - \frac{Q_{ex}}{Q_{CVS}}\right) \cdot Q_{CVS} \right)$$

Over a given sampling interval, all of the above quantities are actually changing with time, so to get the grams over a test phase the time integral is taken:

$$grams_C = Density_C \cdot \left( \int_t [C]_{sam} \cdot Q_{CVS} \cdot dt - \int_t [C]_{amb}\left(1 - \frac{Q_{ex}}{Q_{CVS}}\right) \cdot Q_{CVS} \cdot dt \right)$$

To see how collecting these samples in a bag works to compute these integrals, consider the integral on the left, the sample bag integral. Over the sample interval, a mass of gas is placed in the bag according to the following:

$$grams_{bag} = Density_C \cdot \int_t [C]_{sam} \cdot Q_{bag} \cdot dt$$

Similarly, the volume in the bag at the end of the sample interval is:

$$V_{bag} = \int_t Q_{bag} \cdot dt$$

So the concentration in the bag at the end of the sample interval is:

$$[C]_{sam\_bag} = \frac{\int_t [C]_{sam} \cdot Q_{bag} \cdot dt}{\int_t Q_{bag}}$$

Now, the proper operation of the CVS carefully keeps the sample flow rate and the CVS flow rate precisely proportional to each other, so at all times there is the very important relationship:

$$Q_{bag} = \alpha \cdot Q_{CVS}$$

wherein α is the proportionality constant. Substituting this into the formula above, the α's can be taken out from under the integral and canceled, giving:

$$[C]_{\text{sam\_bag}} = \frac{\int_t [C]_{sam} \cdot Q_{CVS} \cdot dt}{V_{cvs}}$$

This shows that the action of proportionally sampling the mixed, diluted exhaust gases gives exactly the right concentration in the bag to plug into the equation for grams of pollution in place of the integral:

$$grams_C = Density_C \cdot \left( [C]_{\text{sam\_bag}} \cdot V_{CVS} - \int_t [C]_{amb} \left(1 - \frac{Q_{ex}}{Q_{CVS}}\right) \cdot Q_{CVS} \cdot dt \right)$$

Now note however, that the same cannot be done for the second integral, the one that computes the grams of the pollutant that were in the dilution air. This sample bag is not collected under proportional conditions. Conventional CVS methods cannot evaluate this integral precisely. Instead a number of assumptions are made.

First, it is assumed that the ambient concentrations do not change with time and can be taken out from under the integral sign. Then:

$$grams_{amb} = Density_C \cdot [C]_{amb} \int_t \left(1 - \frac{Q_{ex}}{Q_{CVS}}\right) \cdot Q_{CVS} \cdot dt$$

Next, it is assumed that the mass of carbon in the mixed exhaust came only from the vehicle exhaust, so that the ratio of flows in the above can be replaced by the ratio of carbon concentrations in the following manner.

$$grams_{ex}^{carbon} = grams_{mix}^{carbon}$$

$$[Carbon]_{ex} \cdot Q_{ex} = [Carbon]_{CVS} \cdot Q_{CVS}$$

$$\frac{Q_{CVS}}{Q_{ex}} = \frac{[Carbon]_{ex}}{[Carbon]_{CVS}}$$

Then:

$$grams_{amb} = Density_C \cdot \left( [C]_{amb} \cdot V_{CVS} - [C]_{amb} \int_t \frac{[Carbon]_{CVS}}{[Carbon]_{ex}} \cdot Q_{CVS} \cdot dt \right)$$

To continue to evaluate the integral, another assumption is made. It is assumed that the carbon concentration in the exhaust does not change with time, so that it can be taken out from under the integral. Also, since all of the carbon containing gases in the CVS sample are measured, the CVS carbon concentration can be replaced by the sum of these components:

$$grams_{amb} = Density_C \cdot \Bigg( [C]_{amb} \cdot V_{CVS} -$$
$$\frac{[C]_{amb}}{[Carbon]_{ex}} \int_t ([CO_2]_{sam} + [CO]_{sam} + [HC]_{sam}) \cdot Q_{CVS} \cdot dt \Bigg)$$

The items under the integral can now be recognized as the sample bag concentrations times the CVS volume:

$$grams_{amb} =$$
$$Density_C \cdot [C]_{amb} \left( 1 - \frac{[CO_2]_{\text{sam\_bag}} + [CO]_{\text{sam\_bag}} + [HC]_{\text{sam\_bag}}}{[Carbon]_{ex}} \right) \cdot V_{CVS}$$

One further assumption is made: that the combustion is stoichiometric, so that the carbon in the exhaust can be estimated by the formula, (not derived here):

$$[Carbon]_{ex} = \frac{x}{x + \frac{y}{2} + 3.76 \cdot \left(x + \frac{y}{4} - \frac{z}{2}\right)}$$

Substituting this into the above and recognizing that the ratio of carbon concentrations is the dilution factor DF previously described, we finally arrive, after four assumptions which can be questioned in light of the accuracy required today, at the formula used in conventional CVS analysis.

Figure 2:
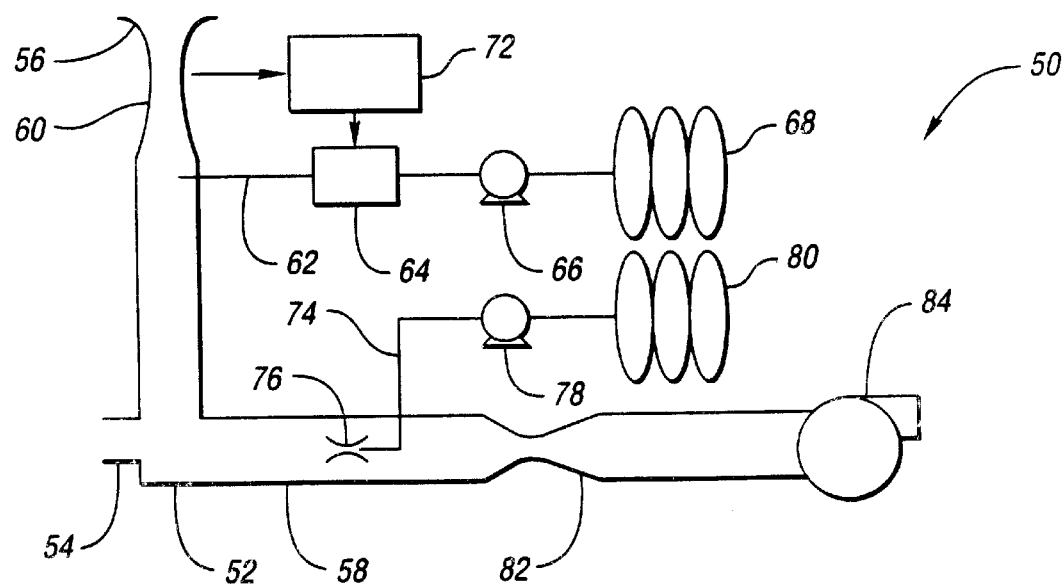
FIG. 2 is a schematic block diagram illustrating a CVS made in accordance with the present invention, and utilizing proportional dilution gas sampling.

Referring to FIG. 2, a mixing system made in accordance with the present invention is generally indicated at 50. Mixing system 50 has a mixing portion 52. A gaseous inlet 54 receives gases, such as exhaust gases, and is in flow communication with mixing portion 52. A dilution inlet 56 receives a dilution gas, which is typical ambient air, and is in flow communication with mixing portion 52. The dilution gas and the test gas form a gaseous mixture at mixing portion 52. The gaseous mixture flows through a mixture outlet 58 in flow communication with mixing portion 52. A flow meter 60 is in flow communication with dilution inlet 56. Flow meter 60 has an output indicative of the dilution gas flow rate. It is to be appreciated that there are many configurations for a flow meter, and that the illustrated flow meter with a flow meter inlet defining a narrowing portion, and a flow meter outlet defining an exit cone is an exemplary form of a flow meter.

A dilution sample line 62 is in flow communication with dilution inlet 56 for collecting samples of the dilution gas. A dilution sample flow controller 64 is located along dilution sample line 62. The dilution sample flow controller, which is preferably a Mass Flow Controller (MFC), is operable to vary the dilution sample flow rate through dilution sample line 62. Sample line 62 may be before or after the flow meter 60. Of course, the relative locations of flow meter 60 and sample line 62 are taken into consideration when calculating the dilution gas flow rate into mixing portion 52 from the flow meter output. A pump 66 is also located along dilution sample line 62. Pump 66 and flow controller 64 cooperate to regulate the flow of the dilution gas into bag 68.

Control logic 72 receives the output from flow meter 60, processes the flow meter output, and operates dilution sample flow controller 64. Control logic 72 operates dilution sample flow controller 64 to vary the dilution sample flow rate in response to variations in the dilution gas flow rate such that the dilution sample flow rate tracks a value which is substantially proportional to the dilution gas flow rate.

Further, a mixture sample line 74 is in flow communication with mixture outlet 58 for collecting samples of the gas mixed at mixture outlet 58. A mixture sample flow controller 76 along mixture sample line 74 is configured to provide a mixture sample flow rate through mixture sample line 74 that is substantially proportional to an overall exiting flow rate at mixture outlet 58. That is, mixture sample line 74 has a flow rate substantially proportional to the flow rate at mixture outlet 58. A pump 78 cooperates with flow controller 76 to draw a gaseous mixture sample into bag 80.

A main outlet flow controller 82 between mixture outlet 58 and a blower 84 regulates the overall exiting flow rate at mixture outlet 58. That is, flow controller 82 cooperates with blower 84 to provide the overall exiting flow rate.

In accordance with the present invention, the inventor has performed mathematical analysis of a preferred embodiment of the present invention. A review of the inventor's mathematical analysis facilitates an overall understanding of a preferred embodiment of the present invention. Accordingly, the inventor's analysis appears below.

To see how the invention improves the evaluation of the integral for the ambient grams, we start with the formula as it applies after the evaluation of the integral for the grams in the sample bag:

$$grams_C = Density_C \cdot \left( [C]_{sambag} \cdot V_{CVS} - \int_t [C]_{amb} \left( 1 - \frac{Q_{ex}}{Q_{CVS}} \right) \cdot Q_{CVS} \cdot dt \right)$$

Note that the term in parentheses in the integral is actually a measure of the dilution air flow:

$$grams_C = Density_C \cdot \left( [C]_{sambag} \cdot V_{CVS} - \int_t [C]_{amb} \cdot Q_{dil} \cdot dt \right)$$

The new sampling method applies the same proportional sampling principle to collect the ambient gases as was applied to the collect the sample gases. That is, we adjust the flow of ambient gases into the ambient bags to keep them proportional to the ambient air flow. In this manner, the concentrations in the ambient bag are given by:

$$[C]_{amb\_bag} = \frac{\int_t [C]_{amb} \cdot Q_{ambbag} \cdot dt}{\int_t Q_{ambbag}}$$

The proportionality condition assures that:

$$Q_{ambbag} = \beta \cdot Q_{dil}$$

which on substitution into the above gives:

$$[C]_{amb\_bag} \cdot V_{dil} = \int_t [C]_{amb} \cdot Q_{dil} \cdot dt$$

Now the simplified and exact formula for the emissions from the vehicle is:

$$grams_C = Density_C \cdot ([C]_{sam\_bag} \cdot V_{CVS} - [C]_{amb\_bag} \cdot V_{dil})$$

wherein $grams_C$ is the gaseous constituent content in the test gas, $density_C$ is the density of the gaseous constituent, $[C]_{sam\_bag}$ is the concentration of the gaseous constituent in the gaseous mixture sample, $V_{CVS}$ is the total volume of the gaseous mixture, $[C]_{amb\_bag}$ is the concentration of the gaseous constituent in the dilution gas sample, and $V_{dil}$ is the total volume of the dilution gas. The modified CVS maintains proportional sampling for both the sample and the dilution air streams, and computes both the CVS volume and dilution air volumes for use in the above formula.

The CVS with proportional ambient sampling offers a number of advantages over conventional methods. It is more accurate because it does not require stable or low ambient concentrations. It does not require a fuel dependent computation of exhaust carbon concentration and the assumption of no water condensation in the vehicle or CVS ductwork. It does not require that the vehicle be operated stoichiometrically, so it is easy to adapt to diesel and gasoline DISI engines. It makes filtering the dilution air with activated charcoal filters unnecessary, avoiding resultant back-pressure (suction) at the connection to the vehicle tailpipe.

Figure 3:
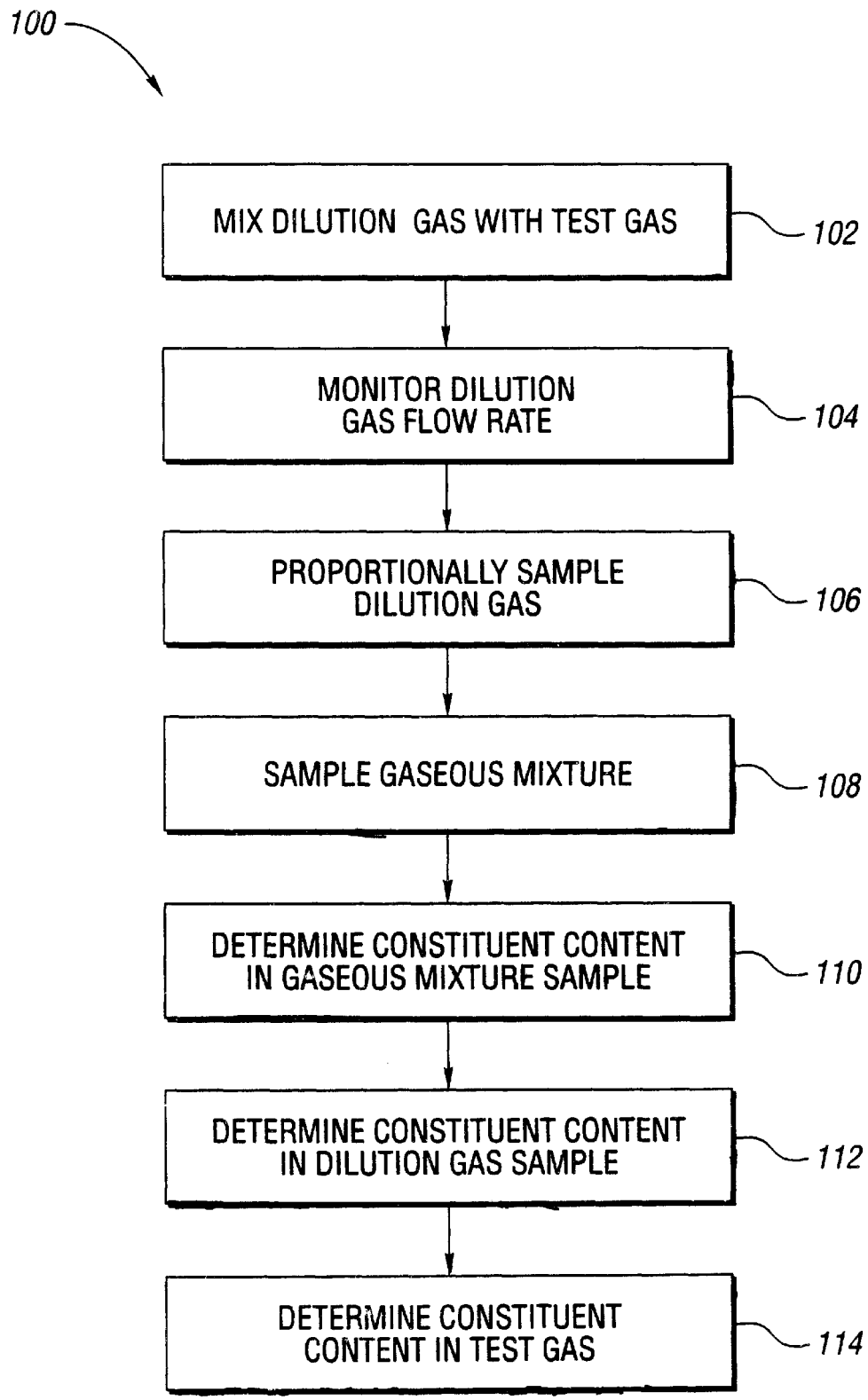
FIG. 3 is a block diagram illustrating a method of the present invention for operating a mixing system, and determining a gaseous constituent content in a test gas.

With reference to FIG. 3, a method of the present invention for operating a mixing system, and for determining a gaseous constituent content in the test gas is generally indicated at 100. At block 102, a dilution gas is mixed with a test gas to produce a gaseous mixture. The dilution gas has a dilution gas flow rate; and, the gaseous mixture has a gaseous mixture flow rate. At block 104, the dilution gas flow rate is monitored. At block 106, the dilution gas is sampled at a dilution sampling rate that is substantially proportional to the dilution gas flow rate to obtain a dilution gas sample. Of course, as mentioned previously, the dilution gas may be sampled either upstream or downstream of the flow meter. At block 108, the gaseous mixture is sampled.

In addition to operating a mixing system in accordance with the present invention as described with reference to blocks 102, 104, 106 and 108, in accordance with the present invention, if desired, the gaseous constituent content of the test gas may be determined. That is, in a preferred embodiment of the present invention, the mixing system is operated as described previously, and further the gaseous constituent content is in the test gas as determined as described below.

With continuing reference to FIG. 3, at block 110, the gaseous constituent content in the gaseous mixture sample is determined. At block 112, the gaseous constituent content in the dilution gas sample is determined. At block 114, the gaseous constituent content in the test gas is determined based on the gaseous constituent contents of the gaseous mixture sample and the dilution gas sample. Preferably, the dilution gas flow rate is monitored with a flow meter having an output indicative of the dilution gas flow rate. Further, in a preferred embodiment, sampling the dilution gas at block 106 is performed by operating a dilution sample flow controller to vary the dilution sampling rate. The dilution sampling rate is varied in response to variations in the dilution gas flow rate such that the dilution sampling rate tracks a value which is substantially proportional to the dilution gas flow rate. Further, preferably, at block 108, the gaseous mixture is sampled at a mixture sampling rate that is substantially proportional to the gaseous mixture flow rate.

Still further, in accordance with a preferred embodiment of the present invention and in accordance with the inventors exemplary mathematical analysis described previously, the gaseous constituent content in the test gas is determined according to:

$$grams_C = Density_C * ([C]_{sam\_bag} \cdot V_{CVS} - [C]_{amb\_bag} * V_{dil})$$

wherein $grams_C$ is the gaseous constituent content in the test gas, $density_C$ is the density of the gaseous constituent, $[C]_{sam\_bag}$ is the concentration of the gaseous constituent in the gaseous mixture sample, $V_{CVS}$ is the total volume of the gaseous mixture, $[C]_{amb\_bag}$ is the concentration of the gaseous constituent in the dilution gas sample, and $V_{dil}$ is the total volume of the dilution gas sample.

While the best mode for carrying out the invention has been described in detail, those familiar with the art to which this invention relates will recognize various alternative designs and embodiments for practicing the invention as defined by the following claims.

What is claimed is:

1. A mixing system for diluting gases, the mixing system comprising:
   a mixing portion;
   a gaseous inlet for receiving the gases, the gaseous inlet being in flow communication with the mixing portion;
   a dilution inlet for receiving a dilution gas at a dilution gas flow rate, the dilution inlet being in flow communication with the mixing portion;
   a mixture outlet in flow communication with the mixing portion;
   a flow meter in flow communication with the dilution inlet, the flow meter having an output indicative of the dilution gas flow rate;
   a dilution sample line with first and second ends the first end being in flow communication with the dilution inlet and configured to sample the dilution gas at a dilution sample flow rate such that a remaining, unsampled, portion of the dilution gas proceeds to the mixing portion and the dilution gas sample remains unmixed for dilution gas analysis at the sample line second end;
   a dilution sample flow controller along the dilution sample line, the dilution sample flow controller being operable to vary the dilution sample flow rate through the dilution sample line; and
   control logic receiving the flow meter output, the control logic processing the flow meter output and operating the dilution sample flow controller to vary the dilution sample flow rate in response to variations in the dilution gas flow rate such that the dilution sample flow rate tracks a value which is substantially proportional to the dilution gas flow rate.

2. The mixing system of claim 1 further comprising:
   a pump along the dilution sample line.

3. The mixing system of claim 1 further comprising:
   a mixture sample line in flow communication with the mixture outlet for collecting samples of a gas mixture at the mixture outlet.

4. The mixing system of claim 3 further comprising:
   a mixture sample flow controller along the mixture sample line, the mixture sample flow controller being configured to provide a mixture sample flow rate through the mixture sample line that is substantially proportional to an overall exiting flow rate of the gas mixture at the mixture outlet.

5. The mixing system of claim 4 further comprising:
   a pump along the mixture sample line.

6. The mixing system of claim 5 further comprising:
   a blower in flow communication with the mixture outlet; and
   a main outlet flow controller between the mixture outlet and the blower, the blower and the main outlet flow controller cooperating to provide the overall exiting flow rate of the gas mixture at the mixture outlet.

7. The mixing system of claim 1 wherein the flow meter has a flow meter inlet defining a narrowing portion and a flow meter outlet defining an exit cone.

8. A method for determining a gaseous constituent content in a test gas using a mixing system, the method comprising:
   mixing a dilution gas with the test gas to produce a gaseous mixture, the dilution gas having a dilution gas flow rate, and the gaseous mixture having a gaseous mixture flow rate;
   monitoring the dilution gas flow rate;
   sampling the dilution gas at a dilution sampling rate that is substantially proportional to the dilution gas flow rate to obtain a dilution gas sample;
   sampling the gaseous mixture to obtain a gaseous mixture sample;
   determining a gaseous constituent content in the gaseous mixture sample;
   determining a gaseous constituent content in the dilution gas sample;
   determining the gaseous constituent content in the test gas based on the gaseous constituent content in the gaseous mixture sample and the gaseous constituent content in the dilution gas sample.

9. The method of claim 8 wherein monitoring the dilution gas flow rate further comprises:
   monitoring the dilution gas flow rate with a flow meter having an output indicative of the dilution gas flow rate.

10. The method of claim 9 wherein sampling the dilution gas further comprises:
    operating a dilution sample flow controller to vary the dilution sampling rate in response to variations in the dilution gas flow rate such that the dilution sampling rate tracks a value which is substantially proportional to the dilution gas flow rate.

11. The method of claim 8 wherein sampling the gaseous mixture further comprises:
    sampling the gaseous mixture at a mixture sampling rate that is substantially proportional to the gaseous mixture flow rate.

12. The method of claim 8 wherein the gaseous constituent content in the test gas is determined according to:

$$\text{grams}_C = \text{density}_C * ([C]_{sam\_bag} * V_{CVS} - [C]_{amb\_bag} * V_{dil})$$

wherein $\text{grams}_C$ is the gaseous constituent content in the test gas, $\text{density}_C$ is the density of the gaseous constituent, $[C]_{sam\_bag}$ is the concentration of the gaseous constituent in the gaseous mixture sample, $V_{CVS}$ is the total volume of the gaseous mixture, $[C]_{amb\_bag}$ is the concentration of the gaseous constituent in the dilution gas sample, and $V_{dil}$ is the total volume of the dilution gas.

13. A method for operating a mixing system, the method comprising:
    mixing a dilution gas with a test gas to produce a gaseous mixture, the dilution gas having a dilution gas flow rate, and the gaseous mixture having a gaseous mixture flow rate;
    monitoring the dilution gas flow rate;
    sampling the dilution gas at a dilution sampling rate that is substantially proportional to the dilution gas flow rate to obtain a dilution gas sample such that a remaining, unsampled, portion of the dilution gas proceeds to mix with the test gas while the dilution gas sample remains unmixed; and
    sampling the gaseous mixture to obtain a gaseous mixture sample.

14. The method of claim 13 wherein monitoring the dilution gas flow rate further comprises:
    monitoring the dilution gas flow rate with a flow meter having an output indicative of the dilution gas flow rate.

15. The method of claim 14 wherein sampling the dilution gas further comprises:
    operating a dilution sample flow controller to vary the dilution sampling rate in response to variations in the dilution gas flow rate such that the dilution sampling rate tracks a value which is substantially proportional to the dilution gas flow rate.

16. The method of claim 13 wherein sampling the gaseous mixture further comprises:

sampling the gaseous mixture at a mixture sampling rate that is substantially proportional to the gaseous mixture flow rate.

17. The method of claim 13 further comprising:

determining a gaseous constituent content in the gaseous mixture sample;

determining a gaseous constituent content in the dilution gas sample;

determining a gaseous constituent content in the test gas based on the gaseous constituent content in the gaseous mixture sample and the gaseous constituent content in the dilution gas sample.

18. The method of claim 17 wherein the gaseous constituent content in the test gas is determined according to:

$$\text{grams}_C = \text{density}_C * ([C]_{sam\_bag} * V_{CVS} - [C]_{amb\_bag} * V_{dil})$$

wherein $\text{grams}_C$ is the gaseous constituent content in the test gas, $\text{density}_C$ is the density of the gaseous constituent, $[C]_{sam\_bag}$ is the concentration of the gaseous constituent in the gaseous mixture sample, $V_{CVS}$ is the total volume of the gaseous mixture, $[C]_{amb\_bag}$ is the concentration of the gaseous constituent in the dilution gas sample, and $V_{dil}$ is the total volume of the dilution gas.

* * * * *